(12) United States Patent
Benkert

(10) Patent No.: US 11,486,952 B2
(45) Date of Patent: Nov. 1, 2022

(54) SYSTEM AND METHOD FOR SELECTING ROTATION ANGLE FOR REDUCED FIELD OF VIEW IMAGING

(71) Applicant: Siemens Healthcare GmbH, Erlangen (DE)

(72) Inventor: Thomas Benkert, Uttenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/065,673

(22) Filed: Oct. 8, 2020

(65) Prior Publication Data
US 2021/0109179 A1    Apr. 15, 2021

(30) Foreign Application Priority Data

Oct. 9, 2019   (EP) .................................... 19202159

(51) Int. Cl.
| | | |
|---|---|---|
| *G01R 33/56* | (2006.01) | |
| *A61B 5/055* | (2006.01) | |
| *G01R 33/385* | (2006.01) | |
| *G01R 33/24* | (2006.01) | |
| *G01R 33/483* | (2006.01) | |
| *G01R 33/54* | (2006.01) | |

(52) U.S. Cl.
CPC .............. *G01R 33/56* (2013.01); *A61B 5/055* (2013.01); *G01R 33/243* (2013.01); *G01R 33/385* (2013.01); *G01R 33/4833* (2013.01); *G01R 33/543* (2013.01)

(58) Field of Classification Search
CPC .... G01R 33/56; G01R 33/243; G01R 33/385; G01R 33/5616; G01R 33/56554; G01R 33/4833; G01R 33/543; G01R 33/4836; A61B 5/055
See application file for complete search history.

(56) References Cited

U.S. PATENT DOCUMENTS

| | | | |
|---|---|---|---|
| 6,188,219 B1 | 2/2001 | Reeder et al. | |
| 2017/0176562 A1* | 6/2017 | Li | ........................ G01R 33/543 |
| 2017/0350951 A1* | 12/2017 | Samsonov | ......... G01R 33/5605 |

OTHER PUBLICATIONS

Banerjee et al., "Reduced Field-of-View DWI with Robust Fat Suppression and Unrestricted Slice Coverage Using Tilted 2D RF Excitation," Magnetic Resonance in Medicine, vol. 76, pp. 1668-1676 (2016).

(Continued)

*Primary Examiner* — Rishi R Patel
(74) *Attorney, Agent, or Firm* — Banner & Witcoff Ltd.

(57) ABSTRACT

In a method for determining imaging parameters for a Magnetic Resonance (MR) image, a set of image sequence parameters of the imaging sequence is determined, a frequency offset of off-resonant tissue potentially present in the object under examination is determined, an allowed maximum position shift of the off-resonant tissue along a slice selection direction is determined, a rotation angle which leads to the allowed maximum shift for the off-resonant tissue is determined based on the determined set of image sequence parameters, and the determined rotation angle is provided to the MR imaging system to allow the MR imaging system to generate the MR image using the determined rotation angle in the imaging sequence.

14 Claims, 2 Drawing Sheets

(56) References Cited

OTHER PUBLICATIONS

Alley et al., "Angiographic Imaging with 2D RF Pulses," Magnetic Resonance in Medicine, vol. 37, No. 2, pp. 260-267 (1997).
Wu et al., "B1 insensitive zoomed FOV imaging," ISMRM—2015, Proc. Intl. Soc. Magnetic Resonance in Medicine, vol. 23 (2015).
Finsterbusch, J., "Improving the Performance of Diffusion-Weighted Inner Field-of-View Echo-Planar Imaging Based on 2D-Selective Radiofrequency Excitations by Tilting the Excitation Plane," Journal of Magnetic Resonance Imaging, vol. 35, pp. 984-992 (2012).
European Search Report dated Apr. 21, 2020 for Application No. 19202159.0.

* cited by examiner

SYSTEM AND METHOD FOR SELECTING ROTATION ANGLE FOR REDUCED FIELD OF VIEW IMAGING

CROSS REFERENCE TO RELATED APPLICATIONS

This patent application claims priority to European Patent Application No. 19202159.0, filed Oct. 9, 2019, which is incorporated herein by reference in its entirety.

BACKGROUND

Field

The present application relates to a method for determining imaging parameters for a Magnetic Resonance (MR) image generated by an MR imaging system of an object under examination in which a part of the object under examination is imaged with a reduced field of view obtained with two dimensionally spatially selective radio frequency (RF) excitation pulses. Furthermore, the corresponding MR imaging system configured to carry out the method, a computer program comprising program code, and a carrier comprising the computer program is provided.

Related Art

Some regions or organs such as the prostate, pancreas or spine are surrounded by tissue several times their size and can, therefore, not be imaged sufficiently and without artifacts with conventional MR techniques. For this purpose, the reduced field of view imaging techniques exist, which are based on two-dimensional RF (2DRF) pulses. Here, only magnetization within a certain predefined area, the field of excitation, is excited.

This technology is based on a two-dimensional RF pulse, where an echo-planar imaging (EPI) trajectory is used to step through excitation k-space while the required RF energy is applied. One direct consequence of this discretized sampling of excitation k-space are side excitations, which occur along the so-called blip direction of the 2DRF pulse. This blip direction can correspond to the phase-encoding direction of the imaging experiment. Accordingly, infolding artifacts can occur when these side excitations are located in tissue.

To overcome these problems, the excitation EPI trajectory can be rotated, which rotates the site lobes out of the phase-encoding direction as disclosed in Jurgen Finsterbusch: "*Improving the Performance of Diffusion-Weighted Inner Field—of-View Echo-Planar Imaging Based on 2D-Selective Radiofrequency Excitations by Tilting the Excitation Plane*", Journal of Magnetic Resonance Imaging, 35:984-992, 2012. Here, the side excitations are not refocused and potential infolding artifacts are effectively overcome.

One side effect of rotating the excitation trajectory is that in the offresonant case, the rotation introduces a shift of offresonant signal components along the slice selection direction. Accordingly, the overlap of these shifted signal components of the examined person with the refocusing pulse is reduced. As a consequence, a certain sensitivity to offresonances ("B0 sensitivity") is introduced. While this B0 sensitivity improves fat suppression and can be beneficial to some extent, it can also lead to unwanted signal decrease in regions with offresonant signal components.

Accordingly, a need exists to overcome the above-mentioned problems of the unwanted signal decrease for the case of the rotated excitation trajectory.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
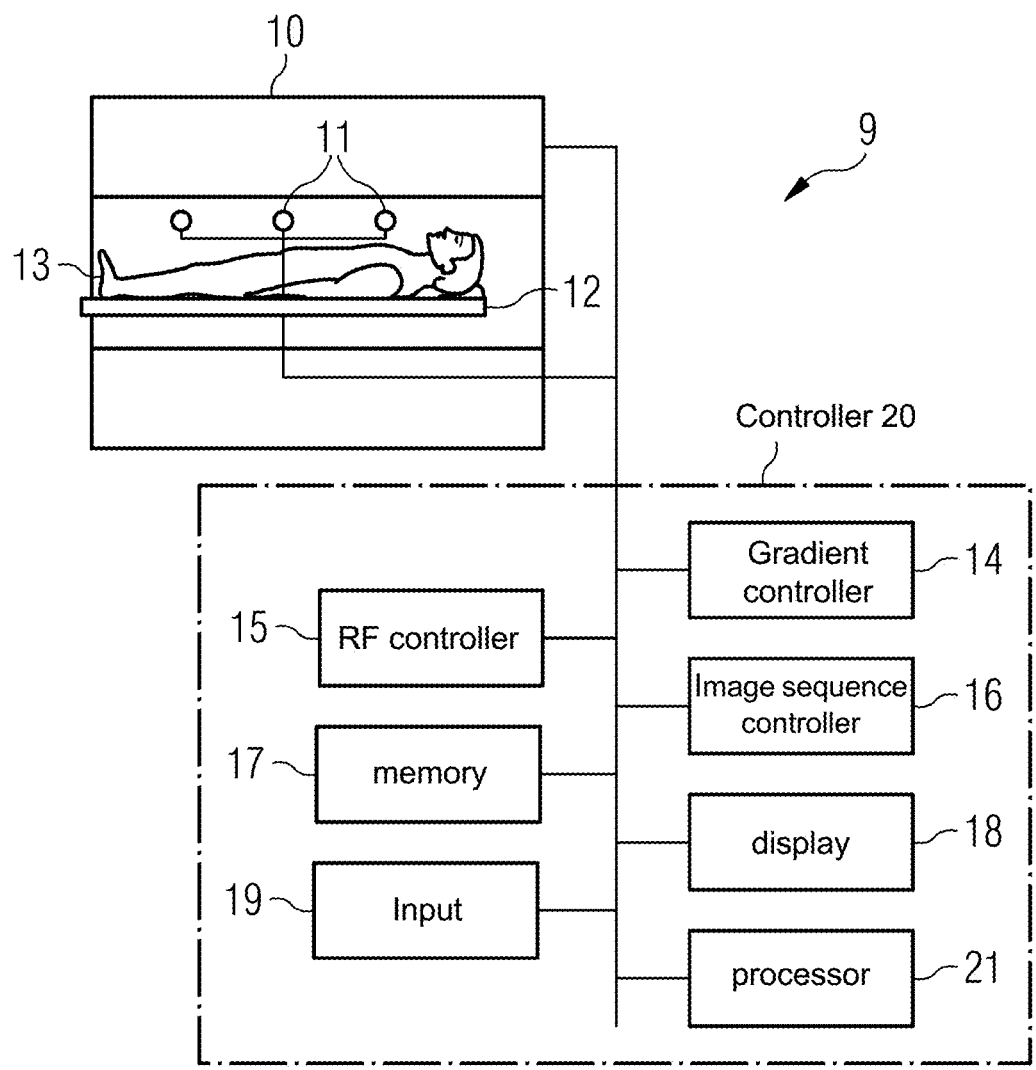
FIG. 1 shows a MR imaging system according to an exemplary embodiment to calculate the rotation angle such that a signal decrease in areas with offresonant tissue is minimized.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

According to a first aspect, a method for determining imaging parameters is provided for an MR image generated by an MR imaging system of an object under examination with an imaging sequence in which a part of the object under examination is imaged with a reduced field of view obtained with 2 dimensional spatially selective RF excitation pulses and magnetic field gradients applied to 2 different directions. Furthermore, the 2 dimensional spatially selective RF excitation pulses are tilted by a rotation angle alpha (different to zero) with regard to an imaging plane where the MR image is generated. According to one step of the method, a set of imaging sequence parameters of the imaging sequence is determined. Furthermore, a frequency offset of offresonant tissue which is potentially present in the object under examination is determined. An allowed maximum position shift of the offresonant tissue is determined along the slice selection direction and the rotation angle which leads to the allowed maximum shift for the offresonant tissue is determined based on the determined set of image sequence parameters, and the determined rotation angle is provided to the MR imaging system in order to allow the MR imaging system to generate the MR image using the determined rotation in the imaging sequence.

With the disclosure the optimal rotation angle which achieves the allowed maximum position shift for a certain frequency offset can be calculated. Accordingly, the situation of the signal attenuation and the offresonant tissue regions is avoided or at least minimized as the attenuation can be selected with the determined allowed maximum position shift.

The step of determining the set of image sequence parameters can include the step of determining the number N of one of the magnetic field gradients applied along one of the two different gradient directions having a smaller gradient moment than the field gradients applied along the other of the two different gradient directions. The rotation angle is then determined taking into account this number N. This direction having the smaller gradient moment is also called the blip direction where blip gradients are used. The determination of the rotation angle includes this number N of blip gradients.

The step of determining the set of image sequence parameters can comprise the step of determining a duration of one of the magnetic field gradients applied along one of the two different gradient directions having a larger gradient moment than the magnetic field gradients applied along the other of the two different directions. The rotation angle is then determined taking into account the determined duration. Here it is the duration of the magnetic field gradients during excitation applied along the other direction, not the blip direction.

Furthermore, the determination of the set of imaging parameters can further comprise the step of determining an extent of the field of view of the MR image in a phase-encoding direction. The rotation angle is then determined taking into account the determined extent of the field of view in the phase-encoding direction.

In an exemplary embodiment, the rotation angle is determined according to the following equation:

Shift=DeltaFrequency*Nblip*DurationLine*FOVphase/ BWTP*sin(alpha)

Here the DeltaFrequency is the frequency offset of the offresonant tissue, the Shift is the allowed maximum position shift of the offresonant tissue, NBlip is the number of blips N, the DurationLine is the duration of the magnetic field gradient in the direction of the gradient having the larger gradient moment, accordingly perpendicular to the blip direction and BWTP is the bandwidths time product, which is the product of the temporal duration of the RF pulse along the blip direction and its spectral width. FOVphase is the field of view in the phase-encoding direction.

The allowed maximum position shift along the slice selection direction may be determined in multiples of a slice thickness in the slice selection direction. Accordingly, the position shift of one slice thickness would mean that this offresonant signal component is completely canceled out or suppressed.

Furthermore, the frequency offset can be determined taking into account a magnetic field strength of the static polarizing magnetic field B0, and can thus made dependent on the field strength such as 20 or 30 Hz/T the field strengths in Tesla. Furthermore, it is possible to determine the frequency offset from a homogeneity map generated for the static polarizing magnetic field B0.

Furthermore, it can be checked whether the determined rotation angle alpha is within a predefined angle range. If this is not the case, the determined rotation angle alpha is amended to a new rotation angle lying in the predefined angle range.

Furthermore, the corresponding MR imaging system is provided comprising a memory and at least one processor. The memory contains instructions executable by the at least one processor. The MR imaging system is operative to work as discussed above or as discussed in further detail below when the instructions are executed by the processor.

Furthermore, a computer program comprising program code to be executed by at least one processor of the MR imaging system is provided, wherein the execution of the program code causes the at least one processor to execute a method as mentioned above or as discussed in further detail below.

Additionally, a carrier comprising the computer program is provided, wherein the carrier is one of an electronic signal, optical signal, radio signal, or computer readable storage medium.

It should be understood that the features mentioned above and features yet to be explained below can be used not only in the respective combinations indicated, but also in other combinations or in isolation without departing from the scope of the present disclosure. Features of the above-mentioned aspects and embodiments described below may be combined with each other in other embodiments unless explicitly mentioned otherwise.

FIG. 1 shows a schematic view of a magnetic resonance (MR) imaging system 9 according to an exemplary embodiment. The MR system 9 is configured to minimize the unwanted signal losses of tissue using a 2DRF imaging technology with a rotated excitation trajectory relative to the imaging plane. The imaging system 9 comprises a magnet 10 configured to generate a polarization field B0. An object under examination 13 lying on a table 12 is moved into the center of the MR system 9 where the MR signal after RF excitation can be detected by receiving coils 11 which can comprise different coil sections and wherein each coil section is associated with a corresponding detection channel. By applying RF pulses and magnetic field gradients, the nuclear spins in the object 13, especially the part located in the receiving coils 11 are excited and the currents induced by the relaxation are detected. The way how MR images are generated and how the MR signals are detected using a sequence of RF pulses and the sequence of magnetic field gradients are known in the art and a detailed description thereof is omitted.

In an exemplary embodiment, the MR system includes a controller 20 which is used for controlling the MR imaging system. The controller 20 comprises a gradient controller 14 for controlling and switching magnetic field gradients, an RF controller 15 configured to control the generation of the 2DRF pulses for the imaging sequences. An image sequence controller 16 is provided which controls the sequence of the applied RF pulses, the magnetic field gradients and the signal detection and thus controls the gradient controller 14 and the RF controller 15. In a memory 17 computer programs needed for operating the MR imaging system and the imaging sequences necessary for generating the MR images can be stored together with the generated MR images. The generated MR images can be displayed on a display 18 wherein an input unit 19 is provided used by a user to control the functioning of the MR imaging system. A processor 21 can coordinate the operation of the different functional units shown in FIG. 1 and can comprise one or more processors which can carry out instructions stored on the memory 17. The memory includes program code to be executed by the processor. Especially the processor can be implemented as disclosed in further detail below to calculate a rotation angle. In an exemplary embodiment, the controller 20 includes processor circuitry that is configured to perform one or more functions and/or operations of the controller 20. One or more components of the controller 20 can include processor circuitry that is configured to perform one or more respective functions and/or operations of the component(s).

Figure 2:
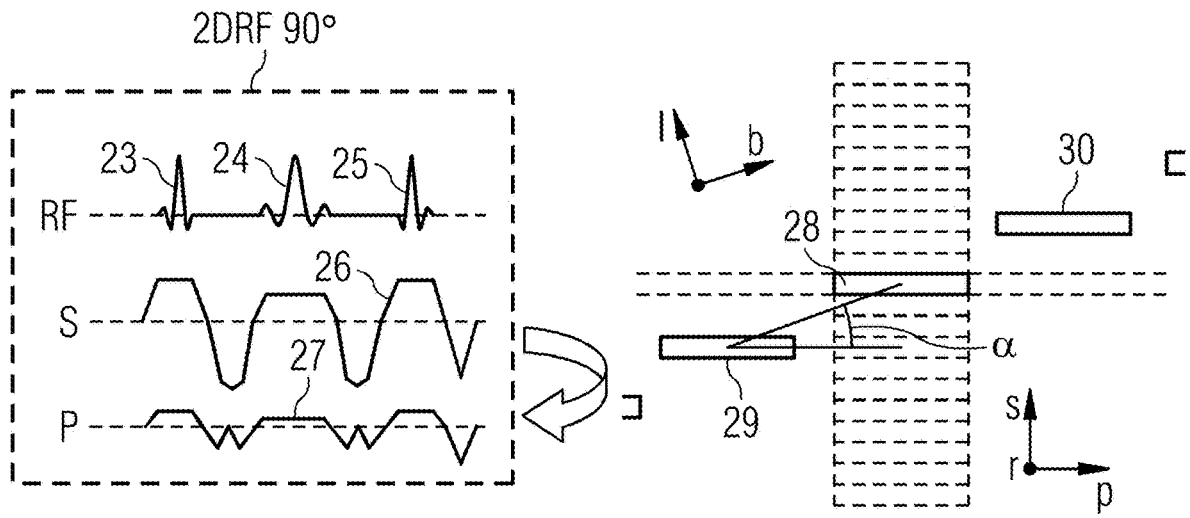
FIG. 2 shows the rotation of the excitation plane which introduces the shift of the offresonant signal components according to an exemplary embodiment.

FIG. 2 shows schematically how the RF excitation is rotated relative to the imaging plane as also described in the above-mentioned document of Finsterbusch in JMRI. The left side of FIG. 2 shows the EPI based two-dimensional RF excitation. As shown the different RF excitation pulses 23, 24 and 25 are applied during the application of magnetic field gradients in a slice selection direction, gradient 26, and the phase-encoding direction, gradients 27. The excitation plane of the 2DRF pulse is tilted such that its blip direction mix up with the imaging slice and phase-encoding direction. In the right part of FIG. 2 the geometric inner field of view 28 is shown together with the side excitations 29 and 30. The slice selection direction S, the phase-encoding direction P and the read-out direction R are shown as indicated. Furthermore, the line direction L of the excitation and the blip direction B are shown. The angle between the blip direction B and the phase-encoding direction P is alpha as shown in FIG. 2. As shown in FIG. 2 the side excitations are positioned in a dead corner between the refocusing RF pulse which is applied within the image section and the slice stack as shown in dashed boxes, wherein the image section is shown in dashed lines. In general it would be also possible to have a rotation angle <0 when the rotations are rotated clockwise instead of counterclockwise as indicated. The 2DRF pulse is used for excitation, while a conventional (e.g. sine) pulse is used as refocusing pulse as known in the art. Offresonant signal components are shifted along the slice direction S and are thus shifted outside the inner field of view 28 which is shown in the image to be generated.

The introduced B0 sensitivity which causes the signal loss depends on the applied rotation angle. For increased rotation angles, the B0 sensitivity is increased. However, applying no rotation angle is not desired either since in this situation, infolding artifacts can occur.

As will be explained below this problem is solved by automatically calculating the rotation angle alpha which limits the induced B0 sensitivity. The goal is to achieve a constant allowed maximum position shift of the offresonant tissue along the slice selection direction across different protocol settings such as the slice thickness etc.

The exact shift can be calculated following equation 9 of Marcus T. Alley et al in "Angiographic Imaging with 2DRF Pulses", Magnetic Resonance in Medicine, MRM 37:260-267, 1997.

The equation is as follows:

$$Shift = DeltaFrequency * Nblip * DurationLine * FOVphase / BWTP$$

Here Shift is the shift in a millimeter of offresonant magnetization with an offresonant frequency of DeltaFrequency, the frequency offset in hertz. Nblip is the number of gradients along the blip direction, the DurationLine is the duration of one line of the excitation k-space along the line direction shown in FIG. 2, the FOVphase is the field of view in the phase-encoding direction and BWTP is the bandwidth time product of the RF pulse along the blip direction.

Based on the situation the rotation angle can be calculated which results in a certain shift of a certain offresonant frequency. Accordingly, the rotation either can be determined as follows:

$$alpha = a\sin(Shift / DeltaFrequency / Nblip / DurationLine / FOVphase * BWTP)$$

One possible implementation is as follows:

The parameters Nblip, DurationLine, the field of view and the bandwidths are predefined by the image sequence parameters and can be inserted directly from the selected imaging sequence. In the next step an empirically defined frequency offset, for example 100 Hertz, is inserted into the equation. This frequency offset can be determined dependent on the field strengths or can be alternatively determined using a measured value which is submitted from the acquired B0 field map.

In the next step an allowed maximum position shift is determined along the slice selection direction which then results in the corresponding signal attenuation or cancellation for the determined frequency offset. This position shift can be implemented in multiples of the slice thickness, one time the slice's thickness, two time the slice's thickness etc.

In the next step the rotation angle can then be calculated from equation 2 mentioned above.

The rotation angle which has been calculated, by way of example for a certain frequency offset and the position shift of one slice thickness would mean that this offresonant signal is canceled or suppressed completely. The tissues with higher frequencies are canceled as well wherein the degree of attenuation for tissue or areas with lower frequency offset would be less.

Figure 3:
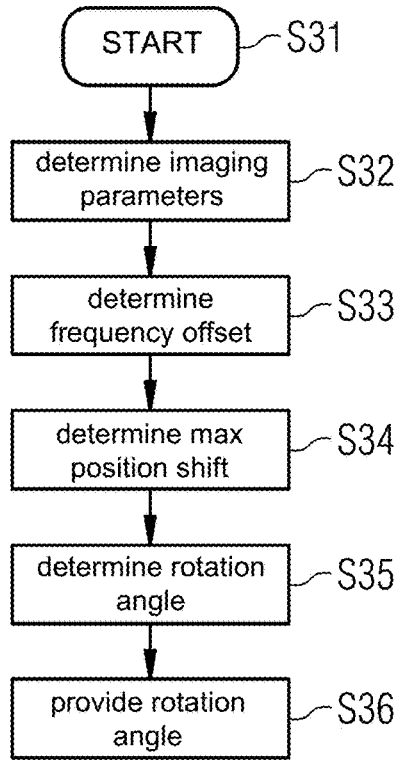
FIG. 3 is a flowchart of a method according to an exemplary embodiment, which can be performed by the MR imaging system of FIG. 1, to determine the rotation angle.

FIG. 3 is a flowchart of a method to determine a rotation angle alpha which provides a constant desired signal attenuation according to an exemplary embodiment. The method starts in step S31 and in step S32 the imaging parameters from the imaging sequence such as the number of blips, the field of view in the phase-encoding direction, the product of the bandwidths with the duration of the gradient applied during the 2D excitation pulses in the line direction can be deduced from the selected imaging sequence. In a step S33 the frequency offset of the offresonant tissue is determined, by way of example a number of hertz. In step S34 the allowed maximum position shift along the slice selection direction is selected and in step S35 the rotation angle is determined using equation 2 mentioned above. The determined angle can then be provided to the MR imaging system so that the MR image can be generated with determined angle.

In step S35 it is also possible that it is checked after the determination of the angle whether the angle is within a certain angle range but by way of example between 5° and 15°. If this is not the case, if a smaller or larger angle may be calculated, a new angle may be selected within the defined angle range With the technology described above stable intensity parameters can be obtained for different imaging parameters as the rotation angle is set such that the attenuation is not larger than a threshold which is defined by the maximum allowed position shift.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for determining imaging parameters for a Magnetic Resonance (MR) image generated by an MR imaging system of an object under examination with an imaging sequence in which a part of the object under examination is imaged with a reduced field of view obtained with 2-dimensional (2D) spatially selective radio frequency (RF) excitation pulses and magnetic field gradients applied to two different directions, wherein the 2D spatially selective RF excitation pulses are tilted by a rotation angle with regard to an imaging plane where the MR image is generated, the method comprising:
   determining a set of image sequence parameters of the imaging sequence;
   determining a frequency offset of off-resonant tissue potentially present in the object under examination;
   determining an allowed maximum position shift of the off-resonant tissue along a slice selection direction;
   determining the rotation angle which leads to the allowed maximum shift for the off-resonant tissue based on the determined set of image sequence parameters; and
   providing the determined rotation angle to the MR imaging system to allow the MR imaging system to generate the MR image using the determined rotation angle in the imaging sequence.

2. The method according to claim 1, wherein determining the set of image sequence parameters comprises determining a number of one of the magnetic field gradients applied along one of the two different directions having a smaller gradient moment than the magnetic field gradients applied along the other of the two different directions, wherein the rotation angle is determined based on the number.

3. The method according to claim 2, wherein determining the set of image sequence parameters further comprises determining a duration of one of the magnetic field gradients applied along one of the two different gradient directions having a larger gradient moment than the magnetic field gradients applied along the other of the two different directions, wherein the rotation angle is determined based on the determined duration.

4. The method according to claim 1, wherein determining the set of image sequence parameters comprises determining a duration of one of the magnetic field gradients applied along one of the two different gradient directions having a larger gradient moment than the magnetic field gradients applied along the other of the two different directions, wherein the rotation angle is determined based on the determined duration.

5. The method according to claim 1, wherein determining the set of image sequence parameters comprises determining an extent of a field of view of the MR image in a phase encoding direction, the rotation angle being determined based on the determined extent of the field of view.

6. The method according to claim 1, wherein the rotation angle is determined according to the following equation:

$$\text{alpha} = a\sin(\text{Shift}/\text{DeltaFrequency}/\text{Nblip}/\text{Duration-Line}/\text{FOVphase} * \text{BWTP})$$

with Shift being the allowed maximum position shift, DeltaFrequency being the frequency offset, Nblip being a number of magnetic field gradients applied along one of the two different directions having a smaller gradient moment than the magnetic field gradients applied along the other of the two different directions, DurationLine being a duration of one of the magnetic field gradients along the gradient direction having a larger gradient moment, FOVphase being the field-of-view in a phase encoding direction, and BWTP being the product of a temporal duration of at least one RF pulse of the 2D spatially selective RF excitation pulses applied during application of the magnetic field gradients applied along one of the two different directions having the smaller gradient moment and a spectral width of the at least one RF pulse.

7. The method according to claim 1, wherein the allowed maximum position shift along the slice selection direction is determined in multiples of a slice thickness in the slice selection direction.

8. The method according to claim 1, wherein the frequency offset is determined based on a magnetic field strength of a static polarizing magnetic field.

9. The method according to claim 1, wherein the frequency offset is determined from a homogeneity map generated for a static polarizing magnetic field.

10. The method according to claim 1, further comprising:
checking whether the determined rotation angle is within a predefined angle range; and
in response to the determined rotation angle being outside the predefined angle range, amending the determined rotation angle to a new rotation angle lying in the predefined angle range.

11. The method according to claim 1, wherein determining the set of image sequence parameters comprises determining a product of: (a) a temporal duration of at least one RF pulse of the 2D spatially selective RF excitation pulses applied during an application of the magnetic field gradients applied along one of the two different directions having a smaller gradient moment than the magnetic field gradients applied along the other of the two different directions, and (b) a spectral width of the at least one RF pulse.

12. A non-transitory computer program product which includes a program and is directly loadable into a memory of the MR imaging system, when executed by a process of the MR imaging system, causes the processor to perform the method as claimed in claim 1.

13. A non-transitory computer-readable storage medium with an executable program stored thereon, that when executed, instructs a processor to perform the method of claim 1.

14. A Magnetic Resonance (MR) imaging system configured to determining imaging parameters for an MR image to be generated by the MR imaging system of an object under examination with an imaging sequence in which a part of the object under examination is imaged with a reduced field of view obtained with 2-dimensional (2D) spatially selective radio frequency (RF) excitation pulses and magnetic field gradients applied to two different directions, the 2D spatially selective RF excitation pulses being tilted by a rotation angle with regard to an imaging plane where the MR image is generated, the MR system comprising:
a memory that stores instructions; and
a processor configured to execute the instructions to:
determine a set of image sequence parameters of the imaging sequence;
determine a frequency offset of off-resonant tissue potentially present in the object under examination;
determine an allowed maximum position shift of the off-resonant tissue along a slice selection direction;
determine the rotation angle which leads to the allowed maximum shift for the off-resonant tissue based on the determined set of image sequence parameters; and
control the MR imaging system to generate the MR image using the imaging sequence.

* * * * *